(12) United States Patent
Ingimarsson

(10) Patent No.: US 7,217,060 B2
(45) Date of Patent: May 15, 2007

(54) PROSTHESIS LOCKING ASSEMBLY

(75) Inventor: Gudni Ingimarsson, Reykjavik (IS)

(73) Assignee: Ossur HF, Reykjavik (IS)

( * ) Notice: Subject to any disclaimer, the term of this patent is extended or adjusted under 35 U.S.C. 154(b) by 141 days.

(21) Appl. No.: 10/835,056

(22) Filed: Apr. 30, 2004

(65) Prior Publication Data

US 2005/0244220 A1 Nov. 3, 2005

(51) Int. Cl.
*F16B 21/00* (2006.01)

(52) U.S. Cl. ............... 403/325; 403/105; 403/107; 403/321; 403/322.1; 403/322.3; 403/324; 623/33; 623/38

(58) Field of Classification Search ............. 403/105, 403/107, 362, 321, 322.1, 322.3, 324, 325; 623/36, 33, 38; 292/160, 172, 252, 279
See application file for complete search history.

(56) References Cited

U.S. PATENT DOCUMENTS

| | | | |
|---|---|---|---|
| 5,507,837 A | | 4/1996 | Laghi |
| 5,779,385 A | * | 7/1998 | Fechter ............ 403/325 |
| 5,888,234 A | | 3/1999 | Littig |
| 6,106,559 A | | 8/2000 | Meyer |
| 6,152,645 A | * | 11/2000 | Sanford ........... 403/322.2 |
| 6,267,787 B1 | | 7/2001 | Capper et al. |
| 6,440,173 B1 | | 8/2002 | Meyer |
| 6,596,027 B2 | | 7/2003 | Laghi |
| 6,596,028 B1 | | 7/2003 | Laghi |
| 6,605,118 B2 | | 8/2003 | Capper et al. |
| 6,626,951 B1 | * | 9/2003 | Gramnas ........... 623/36 |
| 2003/0144744 A1 | | 7/2003 | Grubbs |
| 2004/0030410 A1 | | 2/2004 | Wagman |

OTHER PUBLICATIONS

Ossur, ICELOCK™ clutch 4H 214 L-214000, Instructions for Use.
Ossur, Icelock(r) 200 Series, Product Information, http://www.ossur.com/print.asp?....
Ossur, Product Information, http://www.ossur/com/print.asp?....
Ossur, Icelock™ 200 Series, Version 1, Technical Manual.
Metric Roller Clutches, http://www.sdp-si.com/ss/pdf/sscr7002.pdf.

* cited by examiner

*Primary Examiner*—Daniel P. Stodola
*Assistant Examiner*—Michael P. Ferguson
(74) *Attorney, Agent, or Firm*—Bacon & Thomas, PLLC

(57) ABSTRACT

A locking mechanism includes a centering axle having an engaging member defined at one end thereof, a sleeve encompassing a portion of the centering axle, and a clutch device that securely receives the sleeve and permits rotation of the centering axle and the sleeve in only one direction. The centering axle defines a plurality of equally spaced grooves, and the sleeve defines a plurality of equally spaced grooves corresponding to the grooves of the centering axle in an opposed manner. Each pair of opposed grooves of the centering axle and sleeve define a narrow passageway that accommodates a ball bearing that is slidable along the longitudinal axis of the centering axle and between the sleeve and centering axle. The ball bearing in each passageway permits longitudinal movement of the centering axle relative to the sleeve and prohibits rotation of the centering axle relative to the sleeve.

17 Claims, 5 Drawing Sheets

PROSTHESIS LOCKING ASSEMBLY

BACKGROUND OF THE INVENTION

This disclosure is directed to a locking assembly, and in particular to a locking assembly including a locking mechanism for use in a prosthesis.

A prosthesis is a replacement limb comprised of a plurality of parts. The first component is a liner which is donned by a residual limb. The liner acts as a protective interface between a hard, weight bearing socket and the skin of the residual limb. Once the liner donned on the limb, the residual limb is received by the hard socket. The socket is made to specifically fit the residual limb. The hard socket for a transfemoral prosthesis (above-knee) has a component such as a knee joint connected to it. Below that is an aluminum or carbon fiber tube to which a foot module is connected. A transtibial prosthesis (below-knee) has the foot connected either directly to the hard socket or via a tube, depending on the amputee's height and the length of the residual limb.

Typically, an attachment pin is connected to the distal end of the liner, and engages a locking assembly that may or may not be laminated into the hard socket. The locking assembly is connected to the components connecting to the foot and effectively couples the liner, the hard socket and the components together.

Exemplary conventional locking assemblies are described in U.S. Pat. Nos. 5,507,837, 5,888,234, 6,106,559 and 6,605,118. Conventionally, the attachment pin has a plurality of rack-like notches that extend through a pin bore of a lock body of the locking assembly. The locking assembly is provided with a centering axle having a pinion gear at one end which engages with the notches of the attachment pin to draw the attachment pin into the lock body. The centering axle is mounted within the lock body so as to rotate in only one direction, and is further slidably mounted so as to disengage from the attachment pin upon axially movement within the lock body.

A problem inherent in the conventional locking assemblies is that the centering axle has a tendency to bind with the pinion gear upon wear of the prosthesis and due to the forces applied to the locking assembly by the weight of the user. Such binding of the centering axle with the attachment, in turn, makes it difficult for a user of the prosthesis to release the liner from the hard socket and components connecting to the foot.

SUMMARY

The present invention provides a prosthetic lock assembly that may be used in combination with a prosthesis and which eliminates problems of prior existing lock devices.

In accordance with one feature of the invention, a lock assembly is provided which comprises an attachment lock body having a central bore formed therein and a cylindrical bore extending therein that orthogonally intersects a portion of the central bore, an attachment pin that is connectable to a prosthetic liner, and a locking mechanism that is slidable within the cylindrical bore and configured to engage the attachment pin.

According to one embodiment, the locking mechanism includes a centering axle having an engaging member defined at one end thereof, a sleeve encompassing a portion of the centering axle, and a clutch device that securely receives the sleeve and permits rotation of the centering axle and the sleeve in only one direction. The centering axle defines a plurality of equally spaced longitudinal grooves about its circumference, and the sleeve defines a plurality of equally spaced longitudinal grooves along an inner periphery thereof. The grooves of the sleeve correspond to the grooves of the centering axle in an opposed manner. Each pair of corresponding grooves of the centering axle and sleeve define a narrow passageway that accommodates a ball bearing. The ball bearing is slidable along the longitudinal axis of the centering axle and the sleeve, and therefore permits longitudinal movement of the centering axle relative to the sleeve. The width of the passageway is configured so as to closely resemble the diameter of the ball bearing and thus prohibits rotation of the centering axle relative to the sleeve.

By providing the groove and ball bearing arrangement, the centering axle is able to slide within the lock body in a smoother fashion. The improved operation of the centering axle reduces the amount of force required by a user of the prosthetic lock assembly and facilitates the release of an attachment pin disposed within the lock body.

Additional objects and advantages will be set forth in part in the description which follows, and in part will be obvious from the description, or may be learned by practice. The features of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF VARIOUS EMBODIMENTS

Figure 1:
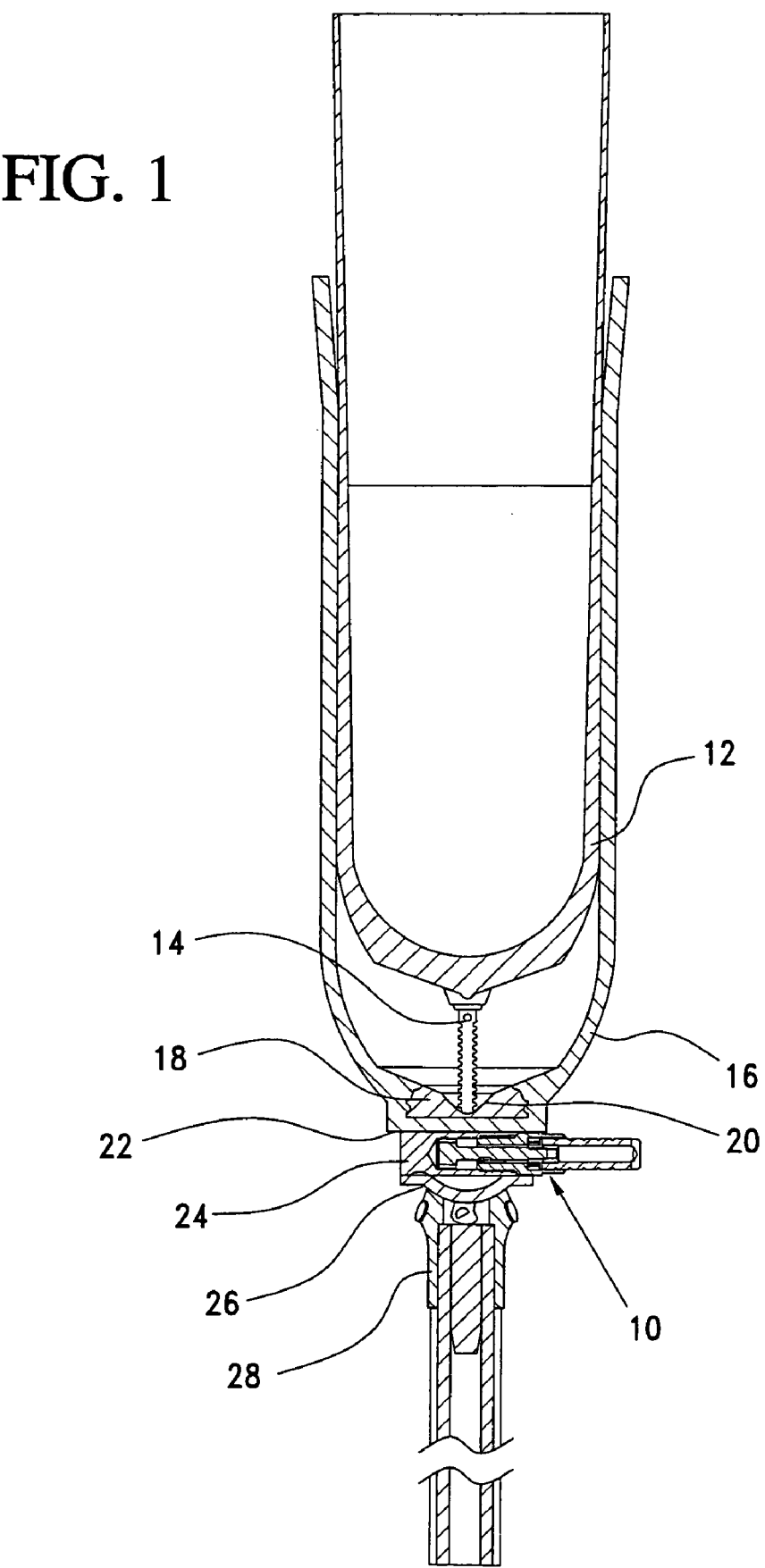
FIG. 1 is a perspective view showing an exploded view of a lock assembly in a prosthesis system.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, and equivalents falling within the spirit and scope of the disclosure as defined by the appended claims.

It will be understood that, unless a term is expressly defined in this patent to possess a described meaning, there is no intent to limit the meaning of such term, either expressly or indirectly, beyond its plain or ordinary meaning.

FIG. 1 illustrates an embodiment of the lock assembly 10 of the invention incorporated into a conventional prosthesis system. A liner 12 is provided which is to be rolled onto a residual limb (not shown) of an amputee. Typical liners are made of soft, stretchy material, such as silicone, and protect the limb and act as an interface between a hard, weight bearing socket 16 and the skin of the limb.

An attachment pin 14 is secured to a distal end of the liner 12 and defines a plurality of notches. The attachment pin 14 may be mounted to the liner 12 by being molded or screwed onto distal end of such liner.

The hard socket 16 includes a lamination ring 18 fitted into the distal end portion thereof with a pin bore 19 extending therethrough and a generally conical taper encircling a region 20 about the pin bore 19. The lamination ring 18 preferably includes a plurality of holes (not shown) extending through the socket 16. The lamination ring 18 may be molded into the socket or sealingly fitted therein. Moreover, a distal end external surface 22 of the socket 18 is generally planar in form.

As illustrated in FIG. 1, the attachment pin 14 connected to the liner 12 is positioned to extend through the central bore 19 of the lamination ring 18 and thus through the socket 16.

Hard sockets are well known in the art of prosthetic devices. Such sockets are configured to accommodate a residual limb donning a liner, such as one described above. A socket having a lamination ring may be manufactured as described in the ICELOCK 200 Series Technical Manual (March 2003), incorporated herein by reference and published by Ossur hf of Reykjavik, Iceland. Alternative devices or methods different from the lamination ring configuration shown herein may also be employed or modified by those skilled in the art of prosthetics to accommodate the embodiments of the lock assembly described herein.

The lock assembly 10 includes a lock body 24 that is positioned below the distal planar surface 22 of the socket 16. The lock body 24 is configured in shape to abut the distal planar surface 22 of the socket 16 and receive the attachment pin 14. Moreover, the lock body 24 preferably includes a plurality of through-holes 25 (as shown in FIG. 2) that may be aligned with the through-holes of the lamination ring 18 and configured to permit fasteners (not shown) to extend therethrough to couple with the lamination ring 18.

The lock body 24 is rigidly secured to lower leg componetry such as a modular pylon system 26, 28. Preferably, the lock body 24 is secured to the lower leg componetry 26 by four screws (not shown) each extending through one of the holes 25 defined at each of four corners of the lock body 24. Exemplary lower componetry includes conventional socket adapters such as those manufactured by Ossur hf of Reykjavik, Iceland under part designations A 233100 (4-Hole Male Pyramid) and A-324100 (Female Pyramid Tube Clamp).

It will be understood, that the prosthetic lock assembly may be integrated with a hard socket, in either a double wall construction socket or integrated into a single wall construction socket during fabrication as discussed and shown in the ICELOCK 200 Series Technical Manual.

Figure 2:
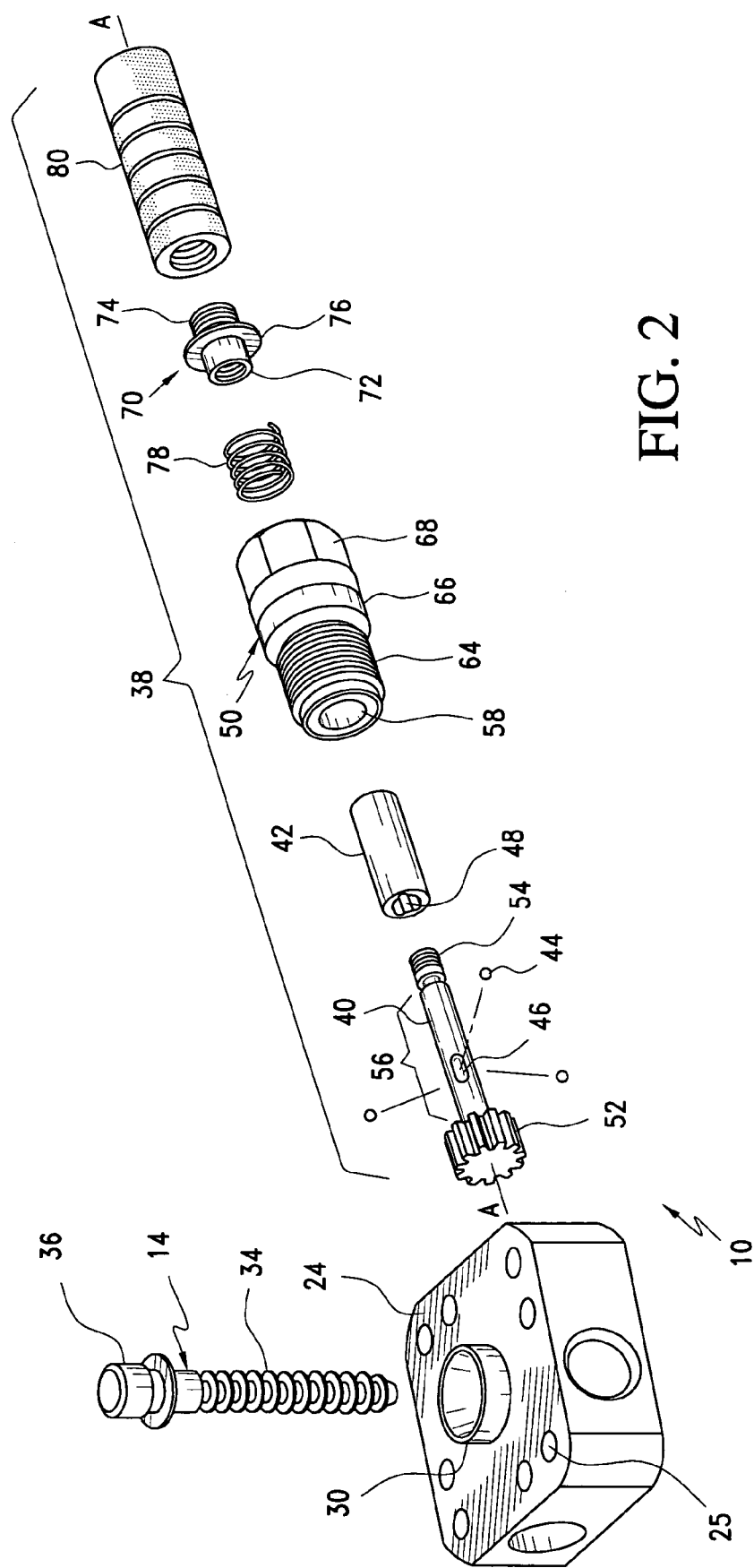
FIG. 2 is an exploded view showing one embodiment of the lock assembly of the present invention.

Referring now to FIG. 2, there is shown an embodiment of the lock assembly 10 of the present invention. The lock assembly 10 includes the lock body 24 having a central bore 30 formed therethrough, and at least one cylindrical bore 32 (shown in FIG. 4) extending therein and intersecting at least a portion of the central bore 30. Preferably, the at least one cylindrical bore 32 extends generally orthogonal to central bore 30.

The lock body 24 may be in the form of a flat disk having a generally rectangular shape with chamfered corners. An example of a conventional lock body is manufactured by Ossur hf of Reykjavik, Iceland and used in the prosthetic lock designated under part name ICELOCK Clutch 214.

A conventional attachment pin 14 is provided for receipt by the central bore 30 of the lock body 24, and includes a plurality of notches 34 formed along the longitudinal length thereof. The notches 34 are preferably axially spaced and define curved a configuration in axial cross-section. The attachment pin 14 includes an upper shank portion 36 arranged for attachment to a liner, such as one described above.

A lock mechanism 38 of the lock assembly 10 is provided to engage and secure the attachment pin 14 within the lock body 24. As shown, the lock mechanism 38 comprises a centering axle 40 for engaging the attachment pin 14, a sleeve 42 encompassing at least a portion of the centering axle 40, a bearing and groove arrangement 44, 46, 48 providing cooperative movement between the sleeve 42 and centering axle 40, and a clutch device 50 arranged to securely receive the sleeve 42 and permit uniform rotation of the centering axle 40 and the sleeve 42. The centering axle 40, the sleeve 42 and the clutch device 50 generally extend along the common axis A—A.

In the exemplary embodiment shown in FIG. 2, the centering axle 40 includes an engaging member 52, located at a first end, such as a pinion gear, located at a first end, a threaded portion 54 located at a second end thereof, and a central portion 56 interposed between the pinion gear 52 and the threaded portion 54. The pinion gear 52 is configured and arranged to engage the attachment pin 14 such that teeth of the pinion gear 52 can mesh with the notches 34 of the attachment pin 14. When the teeth of the pinion gear 52 engage the notches 34 of the attachment pin 14, the pinion gear 52 and the notches 34 of the attachment pin 14 operate in manner similar to a conventional rack and pinion gear system.

The pinion gear 52 may be formed integrally with the centering axle 40, or the pinion gear 52 may connected to the centering axle 40 by means of press fitting or any other suitable means or method available to rigidly secure the pinion gear 52 to the first end of the centering axle 40.

The centering axle 40 defines a least one groove 46 longitudinally extending along the central portion 56. In a preferred embodiment, the centering axle 40 includes three grooves 46 uniformly circumferentially spaced about the periphery thereof, and axially aligned with the longitudinal axis of the centering axle 40. Moreover, the grooves 46 are preferably located at about mid-length of the center portion 56, and have a depth with contours sufficient to accommodate at least a portion of a ball bearing 44. It will be understood, however, that it is preferred that the width of the grooves 46 be sufficiently wide to accommodate the ball bearing 44 yet substantially narrow to prohibit movement of such ball bearing in a direction of such width.

In alternative embodiments, the location of the grooves along the longitudinal axis of the centering axle may be modified so as to be either closer to the first end or the second end thereof. Moreover, appropriate seals or washers may be employed to prevent the balls from departing from the grooves. The seals or washers may be axially aligned with and encircle the centering axle.

In a preferred embodiment, the sleeve 42 is an elongate hollow cylinder that forms a linear bearing for the centering axle 40. As shown more fully in FIGS. 4 and 6, the sleeve 42 is configured in size to slidably encompass a section of the central portion 56 of the centering axle 40. Preferably, the length of the sleeve 42 is less than the longitudinal length of the central shaft portion 56. The centering axle 40 and sleeve 42 are slidable relative to one another between the pinion gear 52 and the threaded end portion 54 of the centering axle 40.

As illustrated in FIG. 2, the sleeve 42 defines along its interior surface at least one groove 48 defined along an inner periphery thereof and located at or near a first end portion intended to be near or adjacent to the pinion gear 52 when the sleeve 42 is positioned on the centering axle 40. The groove 48 of the sleeve 42 is configured in shape to accommodate a sphere. While shown as having a uniform depth, the groove 48 may gradually decrease in depth as it progresses inwardly towards a second end of the sleeve 42 opposite the pinion gear 52 of the centering axle 40.

Preferably, the groove 48 opens at the first end portion of the sleeve and generally has a length greater than the length of the grooves 46 of the centering axle 40. The length of the groove 48 is configured to delimit longitudinal travel of the centering axle 40 relative to the sleeve 42 along axis A—A, and may be modified accordingly depending on the desired length of travel of the centering axle 40.

The sleeve 42 is positioned on the centering axle 40 such that the grooves 48 of the sleeve 42 are aligned with the grooves 46 of the centering axle 40. While the grooves 48 of the sleeve 42 are longer than the grooves 46 of the centering axle, at least a portion of the corresponding the grooves 48 intersect with the grooves 46 to define a longitudinal passageway to receive the ball bearing 44. Preferably the grooves 46, 48 are defined so as to permit the centering axle 40 to move within the sleeve 42 a distance until the pinion gear 52 completely disengages from the notches 34 of the attachment pin 14, and thereby permit the attachment pin 14 to be freely removed from the lock body 24 without impediment.

While a preferred embodiment of the grooves 46, 48 of the centering axle 40 and sleeve 42 has been described, it will be understood that it is within the scope of the invention to modify the position, shape or orientation of such individual grooves, or provide any number of such grooves expedient to one skilled in the art.

In accordance with the preferred embodiment, the ball bearing 44 is seated in each pair of mutually opposed grooves 46, 48 of the centering axle 40 and the sleeve 42, respectively. The ball bearing 44 permits movement of the centering axle 40 along the axis A—A relative to the sleeve 42 and prohibits rotation of the centering axle 40 relative to the sleeve 42.

It will be understood that different bearing elements, such as cylinders, may be provided in place of ball bearings in the passageways formed by grooves 46, 48. Moreover, a plurality of ball bearings may be provided in each of the passageways formed by the grooves 46, 48, as may be deemed useful to one skilled in the art. Moreover, each pair of mutually opposed grooves may have a suitable quantity of a known lubricant to facilitate rolling of the ball bearing disposed therein.

The sleeve 42 is preferably securely received for rotation in one direction within a clutch device 50. The clutch device 50 defines a bore having a first bore portion 58 opening at a first end of the clutch device 50 and includes a plurality of roller elements (not shown) arranged about the inner periphery thereof. The bore of the clutch device 50 includes a second bore portion 62 adjacent the first bore portion 58 and opening to a second end of the bore. The border between the first and second bore portions 58, 62 defines a flange 60 formed as a result of the diameter of the second bore portion 62 being greater in size than the diameter of the first bore portion 58. Unlike the first bore portion 58, the periphery of the second bore portion 62 is generally smooth and devoid of roller elements.

The sleeve 42 is secured within the first bore portion 58 by the plurality of roller elements. The roller elements may be those found in a conventional unidirectional roller clutch such as a roller clutch produced by Stock Drive Products of New Hyde Park, N.Y. under catalog number 599NH3MURCO406. When the sleeve 42 is rotated in one direction, the rollers are configured within the first bore portion 58 to wedge against the outer periphery of the sleeve 42 to prevent further rotation of the sleeve 42. Alternatively, when the sleeve 42 is rotated in an opposite direction, the rollers freely rotate against the sleeve 42. It will be understood that the permitted rotational direction of the sleeve 42 within the clutch device 50 corresponds to a rotational direction in which the pinion gear 52 of the centering axle 40 drives the attachment pin 14 into the lock body 24.

The clutch device 50 defines a first external portion 64 generally corresponding the first bore portion 58 and includes a plurality of external threads arranged for engaging a plurality of internal threads of the horizontal bore of the lock body 24. The clutch device 50 also defines a second external portion 68 located at an end area of the clutch device opposite the first external portion 64. The second external portion 68 defines a nut formed thereof which may be manipulated to release the clutch device 50 from the lock body 24 when the first external portion 64 is threaded thereon. Interposed between the first and second external portions 64, 68 is a flared portion 66 which effectively seals the clutch device 50 onto the lock body 24 when the clutch device 50 is secured thereon.

A coupler 70 is provided which includes a first end 72 having a bore with internal threads, a second end 74 having a plurality of external threads, and a radially extending flange 76 defined between the first end 72 and the second end 74. The first end 72 of the coupler 70 is secured to the threaded end 54 of the centering axle 40. A spring 78 is provided and is engaged between the flange 76 of the coupler 70 and the seat flange 60 of the clutch device 50.

A button 80 is connected to the second end 74 of the coupler 70. As will be discussed more fully in reference to FIGS. 3–6, depression of the button 80 urges travel of the centering axle 40 along the longitudinal axis A—A. Moreover, rotation of the button 80 enables rotation of the centering axle 40 in the direction permitted by the clutch device 50.

The button 80 includes a slot 82 (shown in FIGS. 3 and 5) arranged for accommodating a key, coin, or other suitable engaging means to permit a user to manually rotate the centering axle and thus the pinion. Preferably, the button 80 is made from a plastic which enables a user to easily modify the length of the button by cutting it to an appropriate length.

Figure 3:
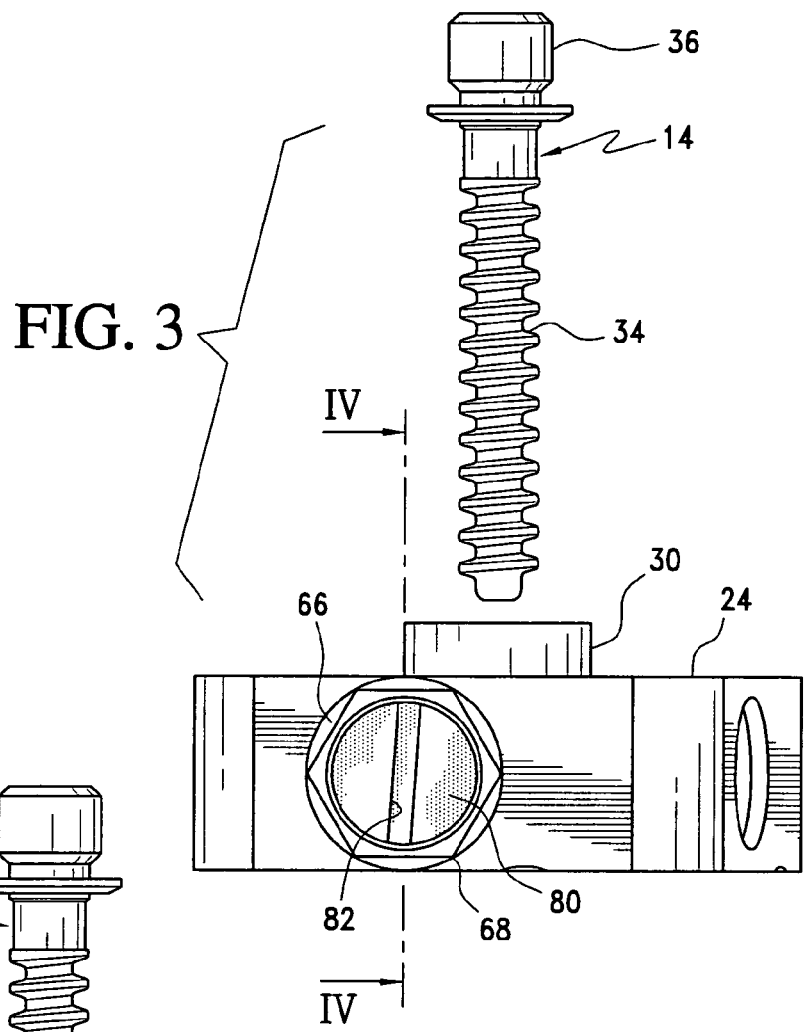
FIG. 3 is an elevational view showing a lock assembly in an unlocked configuration.

Referring to FIGS. 3—6, the basic operation of the lock assembly 10 exemplified in FIG. 2 is shown. In FIG. 3, the attachment pin 14 is shown outside the lock body 24, and is generally axially aligned with the central bore 30.

Figure 4:
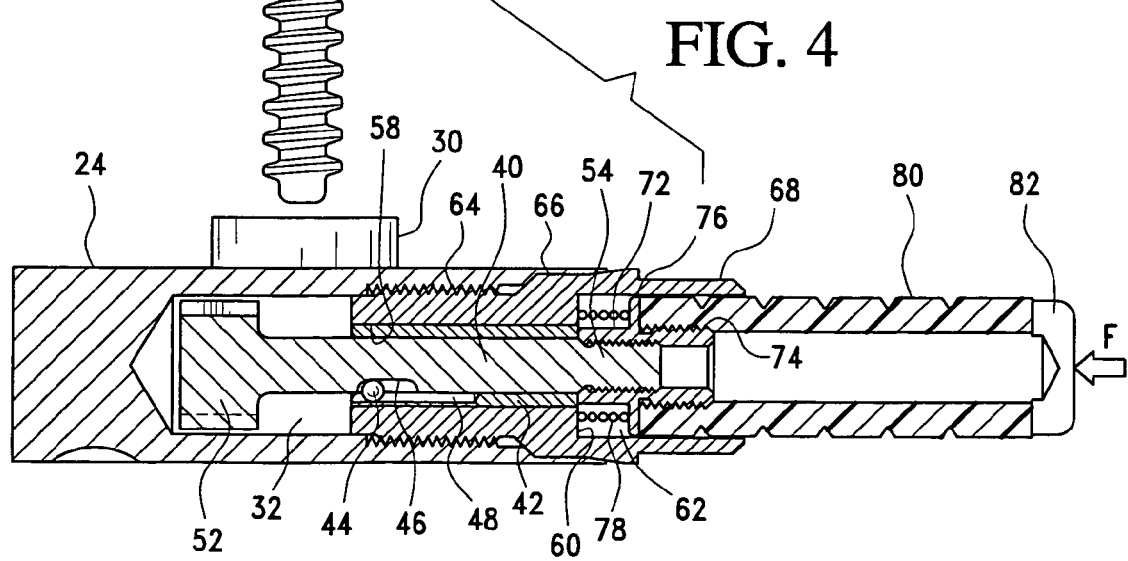
FIG. 4 is a cross-sectional view taken along line IV—IV of the lock assembly of FIG. 3.

As can be seen in FIG. 4, the centering axle 40 is at full extension relative to the sleeve 42. It follows that the ball bearing 44 is located within groove 46 and groove 48 near an end portion corresponding to the side adjacent the pinion gear 52. Moreover, the spring 78 is near completely depressed by the force F exerted on the button 80.

Figure 5:
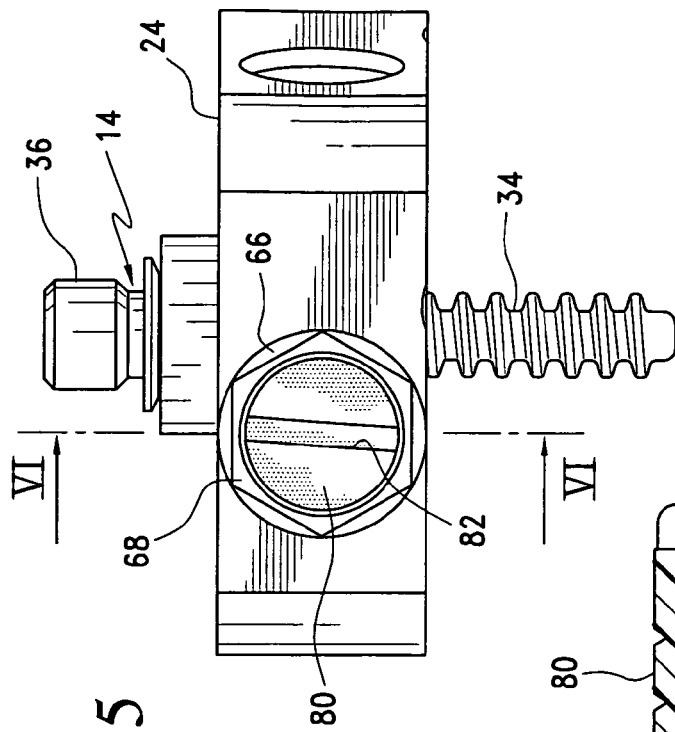
FIG. 5 is an elevational view showing a lock assembly in a locked configuration.
Figure 6:
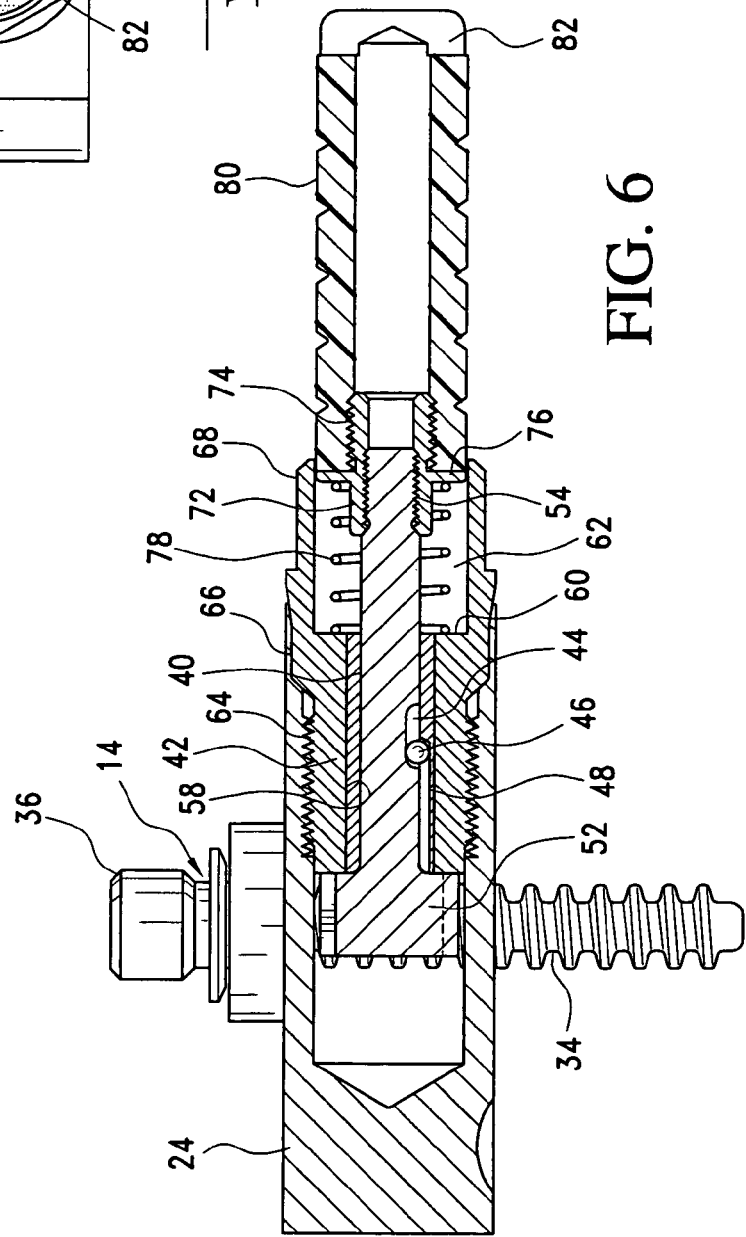
FIG. 6 is a cross-sectional view taken along line V—V of the lock assembly of FIG. 5.

FIGS. 5 and 6 illustrate the lock pin 14 positioned within the central bore 30 of the lock body 24 and is engaged with the pinion gear 52 of the centering axle 40. As exemplified in FIG. 6, the spring 78 biases the centering axle 40 into the position wherein the pinion gear 52 engages the notches 34 of the lock pin 14. Moreover, it will be noted that the centering axle 40 is positioned relative to the sleeve 42 such that the ball bearing is located against a second end of the groove 48 of the sleeve 42 adjacent the spring 78 to prevent further longitudinal movement of the centering axle 40 relative to the sleeve 42.

In the position illustrated in FIGS. 5 and 6, a user can rotate the button 80 so as to rotate the pinion gear 52 to draw the attachment pin 14 into the lock body 24. When it is desired to remove the attachment pin 14 from the lock body 24, a user pushes the button 80 inwardly so as to slidably disengage the pinion gear 52 from the attachment pin 14, as shown in FIGS. 3 and 4. In turn, the attachment pin 14 may freely be withdrawn from the lock body 24 upon disengagement of the pinion gear 52 from the attachment pin 14.

Figure 7:
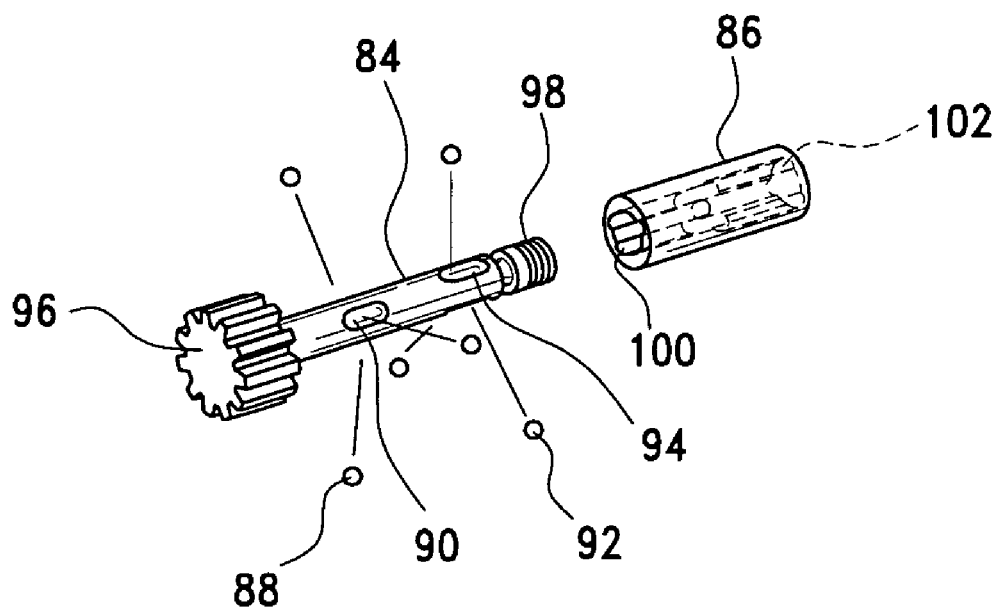
FIG. 7 is an exploded view showing another embodiment of a centering axle and sleeve of the present invention.
Figure 8:
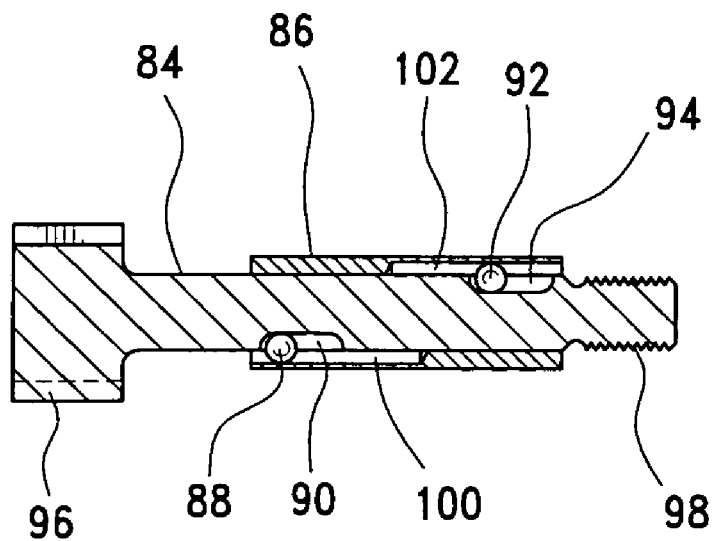
FIG. 8 is a sectional view showing the centering axle and sleeve of FIG. 7 assembled.

FIGS. 7 and 8 show another embodiment of a centering axle 84 and sleeve 86. In this embodiment, the centering axle 84 has an engaging member 96 and a threaded portion 98, and additionally has two sets of grooves 90, 94 positioned about the periphery thereof. The first set of grooves 90 are generally uniformly spaced about a same length segment of the centering axle 84. The second set of grooves 94 are generally uniformly spaced about a different length segment from the first set of grooves 90. Corresponding ball bearings 88, 92 are provided which are sized appropriately to rest within the grooves 90, 94 and be rotatably disposed therein.

The grooves 90, 94 of the centering axle may be defined in a predetermined relationship relative to one another. More particularly, the grooves 90, 94 may be positioned so as to be staggered relative to one another, or may be aligned with one another. Alternatively, there may be no relationship between the grooves 90, 94.

The sleeve 86 is provided with sets of grooves 100, 102 which correspond to the grooves 90, 92 of the centering axle 84. As exemplified in FIG. 8, the grooves 100, 102 of the sleeve 86 are more elongate than the grooves 90, 92 of the centering axle 84. As discussed above, the extra elongation of the grooves 100, 102 permits travel of the centering axle 84 relative to the sleeve 86.

The embodiment presented in FIGS. 7 and 8 provides significant advantages over known prosthetic locking assemblies in that pressure exerted onto the sleeve is transferred to centering axle primarily by the ball bearings, and vice versa. It follows that depending on the depth of the grooves, the centering axle and sleeve may be modified so that there is no contact of the inner surface of the sleeve onto the centering axle. Another advantage to this embodiment is that the pressure is balanced at both ends of the centering axle, thereby preventing jamming of the centering axle at regions between the centering axle and the sleeve near the engaging member or at the threaded portion.

The embodiments of the prosthetic lock assembly of the invention impart significant advantages over known prosthetic lock assemblies. When rotating the centering axle to lock the attachment pin, the load applied to the pinion is transferred to the sleeve which in turn permits the centering axle to move independent of such load. By providing the ball bearings and the corresponding grooves defined along the centering axle and the sleeve, the centering axle is able to move more freely along its axis.

The lock assembly described herein is not limited to use in a prosthesis described in connection with FIG. 1 and may be applied in any suitable application requiring the features of the locking operation described above.

It will be understood that the above described embodiments of the invention are illustrative in nature, and that modifications thereof may occur to those skilled in the art. Accordingly, this invention is not to be regarded as limited to the embodiments disclosed herein, but is to be limited only as defined in the appended claims.

I claim:

1. A lock assembly, comprising:
   an attachment lock body having a central bore formed therein and a cylindrical bore extending therein and orthogonally intersecting at least a portion of the central bore;
   a locking mechanism slidably engaging the cylindrical bore, the locking mechanism including:
   a centering axle including an engaging member at one end thereof, said centering axle including at least one groove defined longitudinally about a circumference along at least a portion of a length thereof;
   a sleeve encompassing a portion of the centering axle and defining at least one groove along an internal periphery thereof and positioned generally opposed to the at least one longitudinal groove of the centering axle, the opposed at least one grooves of the centering axle and the sleeve defining a passageway;
   a slidable ball bearing element positioned in each passageway defined by the grooves of the centering axle and the sleeve, the bearing element sliding within the passageway and permitting longitudinal movement of the centering axle relative to the sleeve and prohibiting rotation of the centering axle relative to the sleeve; and
   a clutch device securely receiving the sleeve and permitting rotation of the centering axle and the sleeve in only one direction.

2. The lock assembly according to claim 1, further comprising:
   a button connected at an end of the centering axle opposite the engaging member; and
   a spring positioned between the button and a surface of the clutch device, said spring biasing the centering axle relative to the sleeve along the longitudinal axis of the centering axle.

3. The lock assembly according to claim 1, wherein the centering axle and the sleeve define three equally spaced passageways.

4. The lock assembly according to claim 3, wherein the clutch device is secured to the periphery of at least a portion of the cylindrical bore of the lock body, said clutch device configured to generally seal the cylindrical bore.

5. The lock assembly according to claim 1, wherein the at least one groove of the sleeve opens at an end thereof facing the engaging member of the centering axle.

6. The lock assembly according to claim 5, wherein the at least one groove of the centering axle is located at a mid-span portion along the longitudinal axis of the centering axle.

7. A locking mechanism, comprising:
   a centering axle including an engaging member defined at one end thereof, said centering axle including at least one groove defined longitudinally about a periphery along at least a portion of a length thereof
   a sleeve encompassing a portion of the centering axle and defining at least one groove defined longitudinally along an inner periphery thereof, each groove of the sleeve slidably opposed to the at least one groove of the centering axle and defining a passageway therewith;

a slidable ball bearing element positioned for sliding within the at least one passageway defined by the centering axle and the sleeve, the bearing element permitting movement of the centering axle along a longitudinal axis relative to the sleeve and prohibiting rotation of the centering axle relative to the sleeve; and a clutch device securely receiving the sleeve and permitting rotation of the centering axle and the sleeve in only one direction.

8. The locking mechanism according to claim 7, wherein the centering axle and the sleeve define three equally spaced passageways.

9. The locking mechanism according to claim 7, further comprising:

a release button connected at an end of the centering axle opposite the engaging member, the release button extending on a side of the clutch device opposite the engaging member; and a spring positioned between the release button and a surface of the clutch device, said spring biasing the centering axle relative to the sleeve along the longitudinal axis of the centering axle.

10. The locking mechanism according to claim 7, wherein the at least one groove of the sleeve opens at an end thereof facing the engaging member of the centering axle.

11. The locking mechanism according to claim 10, wherein the at least one groove of the centering axle is defined at a mid-span location along the longitudinal axis thereof.

12. A lock assembly for releasably connecting a prosthetic device to a sleeve having an attachment pin extending distally therefrom, complying:

an attachment lock body having a central bore formed therein for receiving the attachment pin and a cylindrical bore extending therein and intersecting at least a portion of the central bore;

a locking mechanism slidably engaging the cylindrical bore, the locking mechanism including:

a centering axle including an engaging member at one end thereof configured to engage the attachment pin, said centering axle including at least one groove defined longitudinally about a circumference along at least a portion of a length thereof;

a sleeve encompassing a portion of the centering axle and defining at least one longitudinal groove corresponding to the at least one groove of the centering axle and forming a passageway therewith; and a slidable ball bearing element positioned in each passageway defined by the centering axle and the sleeve, the bearing element sliding within the passageway and permitting movement of the centering axle along a longitudinal axis relative to the sleeve and prohibiting rotation of the centering axle relative to the sleeve.

13. The lock assembly according to claim 12, further comprising a clutch device securely receiving the sleeve and permitting uniform rotation of the centering axle and the sleeve in one direction.

14. The lock assembly according to claim 12, wherein the at least one groove of the sleeve opens at an end thereof facing the engaging member of the centering axle.

15. The lock assembly according to claim 12, wherein the at least one groove of the centering axle is defined along the longitudinal axis thereof at a mid-length portion.

16. A lock assembly for engaging an attachment pin extending from a prosthetic device, the lock assembly comprising:

a centering axle having an engaging member disposed at one end thereof arranged to engage the attachment pin;

a sleeve configured to encompass a portion of the centering axle along the length thereof and axially aligned therewith;

a slidable ball bearing and longitudinal groove arrangement providing cooperation between the sleeve and centering axle due to a relative sliding between the slidable ball bearing and longitudinal groove arrangement;

wherein the bearing and groove arrangement comprises a slidable ball bearing element positioned in a groove defined longitudinally along the circumference of the centering axle and a corresponding groove defined longitudinally along an inner periphery of the sleeve, the bearing element sliding within the groove and permitting movement of the centering axle along a longitudinal axis relative to the sleeve and prohibiting rotation of the centering axle relative to the sleeve and a clutch device securely receiving the sleeve and permitting rotation of the centering axle and the sleeve in only one direction.

17. A lock assembly, comprising:

an attachment lock body having a central bore formed therein and a cylindrical bore extending therein and orthogonally intersecting at least a portion of the central bore;

a locking mechanism slidably engaging the cylindrical bore, the locking mechanism including:

a centering axle including an engaging member at one end thereof, said centering axle including at least two longitudinal groove sets each comprising at least one longitudinal groove defined about a circumference along at least a portion of a length thereof, the at least two longitudinal groove sets positioned along different length segments of the centering axle;

a sleeve encompassing a portion of the centering axle and defining at least two longitudinal groove sets defined along an internal periphery thereof and positioned generally opposed to the at least two longitudinal groove sets of the centering axle, the opposed at least two longitudinal groove sets of the centering axle and the sleeve defining a plurality of passageways;

a slidable ball bearing element positioned in each passageway defined by the longitudinal groove sets of the centering axle and the sleeve, the bearing element sliding within the passageway and permitting longitudinal movement of the centering axle relative to the sleeve and prohibiting rotation of the centering axle relative to the sleeve; and a clutch device securely receiving the sleeve and permitting rotation of the centering axle and the sleeve in only one direction;

wherein the plurality of passageways are equally circumferentially spaced around the circumference of the centering axle and the internal periphery of the sleeve.

* * * * *